(12) United States Patent
Zhang et al.

(10) Patent No.: US 8,747,901 B2
(45) Date of Patent: Jun. 10, 2014

(54) DELAYED RELEASE, ORAL DOSAGE COMPOSITIONS THAT CONTAIN AMORPHOUS CDDO-ME

(75) Inventors: Jiang Zhang, Coppell, TX (US); Colin J. Meyer, Southlake, TX (US)

(73) Assignee: Reata Pharmaceuticals, Inc., Irving, TX (US)

( * ) Notice: Subject to any disclaimer, the term of this patent is extended or adjusted under 35 U.S.C. 154(b) by 267 days.

(21) Appl. No.: 13/201,398

(22) PCT Filed: Feb. 12, 2010

(86) PCT No.: PCT/US2010/024127
§ 371 (c)(1),
(2), (4) Date: Oct. 6, 2011

(87) PCT Pub. No.: WO2010/093944
PCT Pub. Date: Aug. 19, 2010

(65) Prior Publication Data
US 2012/0022156 A1    Jan. 26, 2012

Related U.S. Application Data

(60) Provisional application No. 61/152,608, filed on Feb. 13, 2009.

(51) Int. Cl.
*A61K 9/16* (2006.01)
*A61K 9/50* (2006.01)

(52) U.S. Cl.
USPC ............................................................ 424/490

(58) Field of Classification Search
USPC ............................................................ 424/490
See application file for complete search history.

(56) References Cited

U.S. PATENT DOCUMENTS

2008/0220057 A1    9/2008    Gribble et al.

FOREIGN PATENT DOCUMENTS

| JP | 2008 110962 A | | 5/2008 |
|---|---|---|---|
| JP | 2008-247898 A | | 10/2008 |
| WO | WO-2008/111497 A1 | | 9/2008 |
| WO | WO 2009/023232 | * | 2/2009 |
| WO | WO 2009/023232 A1 | | 2/2009 |
| WO | WO 2009/089545 A1 | | 7/2009 |

OTHER PUBLICATIONS

Lewis et. al. (Pak. J. Pharm. Sci. (2009) 22:234-246).*
International Search Report PCT/US2010/024127 dated Jun. 17, 2011.
Database WPI Week 200869 Thomson Scientific, London GB; AN 2008-L86128 XP002640919 & WO 2008/111497 A1 (Santen Pharm Co Ltd) Sep. 18, 2008 *Abstract.
Singapore Patent Application No. 201105712-2—Written Opinion and Search Report dated Dec. 19, 2012.
China Application No. 201080007105X—Office Action dated Nov. 14, 2012.
Korean Intellectual Property Office Notice of Non-Final Rejection for Application No. 10-2011-7021250 dated Nov. 26, 2013.
Serajuddin, "Solid Dispersion of Poorly Water-Soluble Drugs: Early Promises, Subsequent Problems, and Recent Breakthroughs", Journal of Pharmaceutical Sciences, vol. 88, No. 10, Oct. 1999, pp. 1058-1066.

* cited by examiner

*Primary Examiner* — Marcos Sznaidman
(74) *Attorney, Agent, or Firm* — Foley & Lardner LLP

(57) ABSTRACT

Pharmaceutical formulations exhibit a desirably low Cmax, among other properties, that contain particles of amorphous bardoxolone methyl, either in pure form or in the form of a solid dispersion, admixed with particles of a hydrophilic binding agent. Such formulations possess the advantage of higher oral bioavailability, relative to formulations based on the crystalline form of bardoxolone methyl.

11 Claims, 2 Drawing Sheets

DELAYED RELEASE, ORAL DOSAGE COMPOSITIONS THAT CONTAIN AMORPHOUS CDDO-ME

CROSS-REFERENCE TO RELATED APPLICATIONS

This application claims the benefit under 35 U.S.C. §119 (e) of U.S. Provisional Application Ser. No. 61/152,608, filed Feb. 13, 2009, the content of which is incorporated by reference into the present disclosure in its entirety.

BACKGROUND OF THE INVENTION

The synthetic triterpenoid bardoxolone methyl, also known as CDDO-Me and as "RTA 402," has shown potent anti-inflammatory and anti-tumor properties in preclinical studies and in human clinical trials. In particular, bardoxolone methyl has shown significant anticancer activity in patients with advanced cancer, and has shown the ability to improve measures of kidney function, insulin resistance, glycemic control, and systemic cardiovascular disease in patients suffering from chronic kidney disease as a result of Type 2 diabetes.

In these studies bardoxolone methyl was administered orally in a crystalline form ("Form A"), once daily, at a variety of doses. In addition to the significant clinical efficacy noted in these studies, Form A bardoxolone methyl showed an excellent tolerability profile with very few drug-related side effects noted.

Pharmacokinetic data from these studies indicated, however, that Form A bardoxolone methyl has relatively low oral bioavailability. Fortunately, a non-crystalline form of bardoxolone methyl ("Form B") also has been identified, which shows markedly superior oral bioavailability compared to Form A.

It is well understood that improved oral bioavailability is a desirable feature of a drug formulation, since it reduces the per-dose cost of active material and is consistent with the general medical principle of administering the lowest amount of a drug that is known to produce the desired effect. Conversely, low aqueous solubility resulting in poor oral bioavailability of potential drug candidates has been recognized as a significant challenge facing the pharmaceutical industry.

In fact, an estimated 25-30% of compounds in early development have poor bioavailability due to low solubility. The United States Food and Drug Administration has adopted a biopharmaceutics classification system (BCS) that classifies drugs intended for oral dosage according to solubility and membrane permeability. Drugs that are poorly soluble yet highly membrane permeable make up a substantial portion of drug candidates and are referred to as BCS class 2 drugs. For this class of drugs intended for oral dosage, improvements in effective bioavailability can occasionally be addressed by altering the solubility profile of the drug substance, either alone or via the use of functional excipients in an appropriate pharmaceutical composition.

Several techniques have evolved to improve the solubility of certain drug candidates that have the potential to be safe and effective. One such technique that has been explored is to formulate the drug using an amorphous form of the drug substance, either alone or in a polymer matrix. While improvements in aqueous solubility of amorphous forms over that of the corresponding crystalline forms of the drug substance have been documented, such systems are inherently unstable and may return to their thermodynamically more stable crystalline state. As a result, considerable research and experimentation often is conducted to define formulation systems that can yield formulations with acceptable shelf-life.

Because dissolution rates and solubility in physiological media are typically higher in the upper gastrointestinal system, formulations containing amorphous drug substances, if they can be developed, often behave differently in vivo, relative to those formulations containing the corresponding drug in a crystalline form. Formulations containing amorphous drug substances have been reported to produce bioavailability enhancements and have area-under-curve (AUC) values several-fold higher than formulations containing the corresponding crystalline form of the drug substance on an equivalent dose basis. While it is not unusual for amorphous forms of drugs, once absorbed into general circulation, to exhibit similar metabolism, distribution, and excretion profiles, the time to maximal plasma concentration (Tmax) and the maximal concentration observed (Cmax) often are altered markedly in formulations containing amorphous drugs compared to their crystalline counterparts.

If a drug exhibits toxicity or is associated with an increased frequency of adverse events above a certain limiting plasma concentration, then maintaining therapeutic plasma levels safely below such a limiting level may be of paramount importance. Thus, even if a drug has a broad therapeutic window and is otherwise safe and effective, the control of Cmax or Tmax profiles may be important if the drug is to be administered chronically. More generally, if a particular plasma concentration profile is associated with a desirable profile of safety and efficacy, it is useful for alternative formulations containing the same active ingredient to produce a comparable plasma concentration profile.

SUMMARY OF THE INVENTION

In view of the foregoing, the present invention provides, according to one of its aspects, a solid dosage form comprising (A) particles comprised of amorphous bardoxolone methyl admixed with (B) particles comprised of at least one hydrophilic binder, such as a cellulose-based excipient, where the particles (A) constitute a therapeutically effective amount of bardoxolone methyl. Illustrative of the class of suitable cellulose-based excipients are: $C_3$-$C_{10}$ alkyl hydroxymethyl cellulose, e.g., methyl cellulose, ethyl cellulose, propyl cellulose, hydroxymethyl cellulose, hydroxypropyl cellulose, hydroxypropyl methyl cellulose, and cellulose acetate; aryl hydroxymethyl cellulose; and substituted aryl hydroxymethyl cellulose. Alternatively, the hydrophilic binder may be a naturally occurring carbohydrate polymer or an anionic polymer.

In one embodiment of the invention, the particles (A) consist essentially of amorphous bardoxolone methyl. In another embodiment, the particles (A) are comprised of a solid dispersion of amorphous bardoxolone methyl in a glassy matrix, which can be obtained, for example, as the product of a process that comprises spray drying a mixture of bardoxolone methyl and a methacrylic acid copolymer. Such spray drying can involve, for instance, using a 4:6 mixture of bardoxolone methyl and a methacrylic acid copolymer.

In accordance with this invention, the proportion of the hydrophilic binder in a solid dosage form as described here may be between about 1% and about 40% (w/w) of the total formulation, e.g., between about 2% and about 20% (w/w), about 4% and about 10% (w/w), about 5% and about 7.5% (w/w), or about 7% and about 7.5% (w/w) or at about 7% (w/w) of the total formulation.

Formulations of the present invention exhibit modified Cmax profiles relative to formulations that lack hydrophilic binding agents. More particularly, an inventive formulation produces a significantly lower Cmax than that obtained with a comparable formulation containing the amorphous dispersion but lacking the hydrophilic binding agent. The inventive formulation maintains the advantage of higher oral bioavailability compared to formulations based on the crystalline form of bardoxolone methyl.

DETAILED DESCRIPTION OF THE PREFERRED EMBODIMENTS

Figure 1:
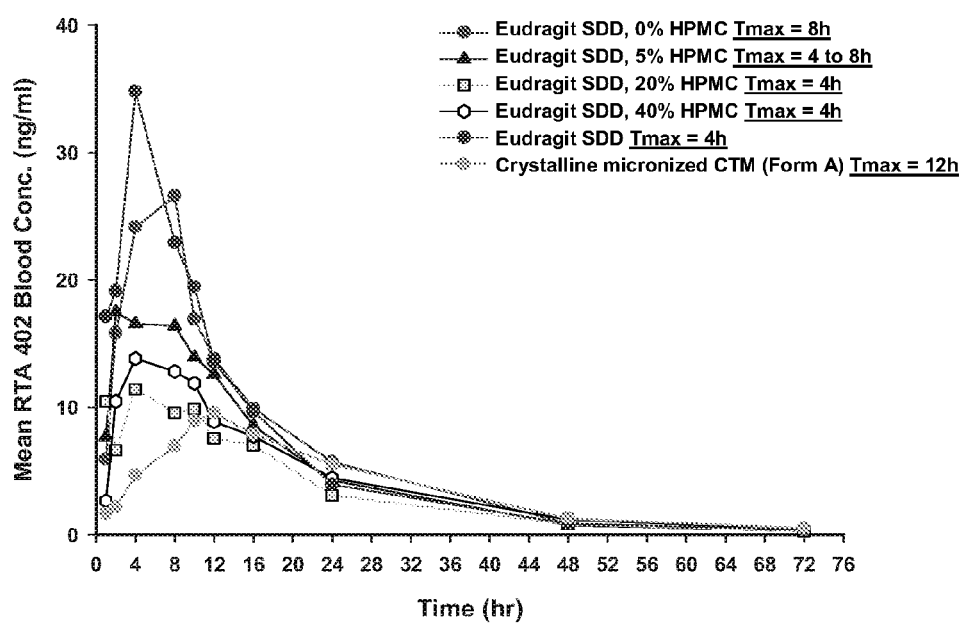
FIG. 1 is a graphical representation of bioavailability data obtained via single-dose oral administration of different RTA-402 formulations to cynomolgus monkeys.

Preclinical studies with various formulations containing an amorphous dispersion of bardoxolone methyl (Form B) indicate that its improved oral bioavailability was associated with significantly increased Cmax relative to Form A material, as well as with an overall plasma concentration curve that differs markedly from that of Form A in equivalent doses. In view of the significant efficacy and excellent tolerability obtained with Form A bardoxolone methyl in clinical studies, the present inventors sought to identify a formulation containing an amorphous dispersion of bardoxolone methyl that would maintain the advantage of improved oral bioavailability while producing a plasma concentration curve more closely resembling that associated with Form A. This would afford greater confidence that the efficacy and tolerability profile of such a formulation in subsequent clinical studies would be consistent with that observed in studies using Form A material.

By virtue of this investigation, the present inventors discovered that a modified formulation of a solid dispersion of bardoxolone methyl, containing as an additive one or more hydrophilic binding agents, for example, cellulose-based binders, such as hydroxypropyl methyl cellulose, showed the desired properties. These hyrdophilic binding agents are believed to modulate dissolution rate, providing not only oral bioavailability that is several-fold greater than that of Form A material but also, following oral dosing, a lower Cmax than previous Form B formulations. Consequently, a formulation of the invention yields an overall plasma concentration curve (PCC) that more closely resembles the PCC associated with Form A material.

In animal studies, formulations based on a micronized solid dispersion of Form B admixed with hydrophilic binder showed significantly higher Cmax values, relative to formulations containing equivalent doses of crystalline bardoxolone methyl. Thus, addition of the hydrophilic binder does not negate the superior bioavailability of such amorphous forms of bardoxolone methyl, in comparison with crystalline forms.

Qualitatively similar results should pertain as well for a formulation, according to the invention, of pure Form B particles admixed with particles of a hydrophilic binder. In this context, "pure" connotes the presence of amorphous bardoxolone methyl free of any material, including an excipient, that could affect the pharmaceutical properties of the drug. This use of "pure" is intended not to denote absolute purity; rather, it comports with the normal standard of acceptable purity for a pharmaceutical agent. A synonymous phrasing in this regard qualifies particles of an inventive formulation as "consisting essentially of" Form B. In a solid dispersion that is comprised of Form B, a glass-forming excipient constitutes a significant percentage of the total material and is important in determining overall pharmacological properties.

Each non-crystalline form of bardoxolone methyl, whether pure Form B or a solid dispersion containing Form B combined with a glass-forming excipient, is characterized by a single glass transition temperature (Tg), which can be measured via differential scanning calorimetry. Each non-crystalline form of bardoxolone methyl also has a characteristic, broad halo peak, observed by X-ray powder diffraction (XRPD), which is indicative of the presence of an amorphous form.

A solid dispersion of bardoxolone methyl employed in accordance with one aspect of the present invention may be produced with any of various glass-forming materials, used as excipients. Thus, one embodiment of the invention is a formulation in which particles of such a solid dispersion of bardoxolone methyl are admixed with particles of a hydrophilic binder, optionally with particles of other excipients. The resulting admixture, when administered to a subject by oral dosing or other means, produces a modified plasma concentration curve compared to formulations containing the same amount of the solid dispersion of bardoxolone methyl but lacking the hydrophilic binder.

This modified plasma concentration curve is characterized by a lower Cmax relative to the formulation that lacks the hydrophilic binder. By the same token, admixing particles of pure Form B bardoxolone methyl with particles of a hydrophilic binding agent, pursuant to another aspect of the invention, yields similar effects on the plasma concentration curve. A lower Cmax is manifested, that is, relative to an equivalent formulation lacking the hydrophilic binder.

A variety of preparative techniques can be used to produce solid dispersions of amorphous bardoxolone methyl, pursuant to this invention. Suitable in this regard, for example, is a variety of conventional thermal methods (e.g., hot melt extrusion), solvent methods, and thermal/solvent methods (e.g., spray drying or fluidized bed coating of granules).

Also suitable in accordance with the invention are ratios of bardoxolone methyl, the active ingredient, to the glass forming excipient that are other than the 4:6 ratio referenced below. As a function of the glass forming excipient and production methodology employed, suitable ratios can vary significantly, ranging, for example, between about 1:19 and about 2:1.

As noted above, any of a variety of glass forming excipients are suitable for use in the invention, so long as the given excipients can form a glassy solid matrix, having a glass transition temperature (Tg). Illustrative of such excipients are derivatives of cellulose (e.g., hydroxypropyl cellulose), acrylic acid derivatives and other synthetic polymers (e.g., polyvinyl pyrrolidone and copovidone), organic acid salts, and proteins and peptides (e.g., albumin and polyalanine).

A solid dosage form of the invention may be administered by other than oral dosing. These other, suitable administration routes include but are not limited to nasal, pulmonary, transmucosal, and transdermal delivery.

Solid dispersions of Form B (amorphous) bardoxolone methyl have exhibited superior oral bioavailability compared to formulations containing pure Form B bardoxolone methyl (data not shown). Still, both types of amorphous material have displayed dramatically improved oral bioavailability compared to crystalline forms of bardoxolone methyl. Accordingly, the present invention encompasses, in one of its aspects, a formulation that contains pure Form B bardoxolone methyl admixed with one or more hydrophilic binding agents, such that the admixture achieves an overall plasma concentration profile similar to the formulations exemplified below. Such admixing does not yield a solid dispersion, regardless of whether the hydrophilic binder could serve as a glass-forming excipient in another context. This is so because the admixing process according to the invention does not involve steps, e.g., dissolving both materials in a solvent and then spray-drying, that are required for the formation of a solid dispersion.

A formulation containing pure Form B bardoxolone methyl, pursuant to the invention, may require different proportions of hydrophilic binder to active, compared with a formulation containing a solid dispersion of Form B, in order to achieve the desired plasma concentration profile. For instance, a lower amount of hydrophilic binder versus active ingredient might be required to compensate for the lower bioavailability of pure Form B material, relative to a solid dispersion containing a comparable amount of Form B material, as described above. More generally, either lower or higher proportions of hydrophilic binder(s)-to-active might be required to achieve the desired results with pure Form B material, depending on the nature of the hydrophilic binding agent or agents employed and the effects of other excipients that may be present in the formulation.

A dosage form of the invention typically contains a therapeutically effective amount of amorphous bardoxolone methyl. In this regard, an amount that is "therapeutically effective" is sufficient to activate the Nrf2 signaling pathway in circulating blood cells. See Ichikawa et al., (2009) PloS One, 4(12):e8391. More generally, a therapeutically effective amount can be determined empirically, by reference to a patient's clinical parameters.

To illustrate the invention, amorphous bardoxolone methyl-containing compositions were prepared as a spray-dried dispersion (SDD). A solid dispersion of Form B, each of the SDD compositions was produced by spray-drying solutions that contained a 4:6 ratio of bardoxolone methyl (Form B) to a glass-forming excipient, methacrylic acid copolymer Type C, USP. A formulation was prepared by blending the resultant particles of a given SDD with a hydrophilic binding agent, such as hydroxypropyl methyl cellulose, together with other excipients, as shown below in Table 1, followed by roller compaction of the blend, milling, and encapsulation of the granules thus obtained.

In general terms, the final product of this exemplary process was a mixture in granular form, each granule containing (i) particles of an amorphous dispersion containing Form B bardoxolone methyl, (ii) particles of the hydrophilic binder(s), and (iii) particles of the other excipients. An analogous process could be used, varying in the nature of the starting material, i.e., pure Form B rather than a solid dispersion containing Form B, to produce a mixture in granular form. In this instance, each granule would contain (1) particles of pure Form B, (2) particles of the hydrophilic binder(s), and (3) particles of the any other excipient(s).

As shown in Table 1, reference "formulation #1" (identified in FIG. 1 as "Eudragit SDD") contained copovidone, a disintegration agent. Modifications to the reference formulation, each modification containing no copovidone, were produced and contained from 0% to 40% by weight of hydroxypropyl methylcellulose (HPMC), a representative of the cellulose-based hydrophilic binder subclass. Percentages of the excipients lactose and microcrystalline cellulose were adjusted downward accordingly (Table 1).

TABLE 1

Composition of control formulation and formulation modifications containing hydroxypropylmethyl cellulose

| Components | #1 | #2 | #3 | #4 | #5 |
|---|---|---|---|---|---|
| Bardoxolone methyl (SDD) | 12.50% | 12.50% | 12.50% | 12.50% | 12.50% |
| Microcrystalline Cellulose | 20.00% | 29.00% | 24.00% | 29.20% | 22.50% |
| Lactose Monohydrate | 53.50% | 53.50% | 53.50% | 33.30% | 20.00% |
| Copovidone XL | 9.00% | 0.00% | 0.00% | 0.00% | 0.00% |
| Sodium Lauryl Sulfate | 3.00% | 3.00% | 3.00% | 3.00% | 3.00% |
| Colloidal Silicon Dioxide | 1.00% | 1.00% | 1.00% | 1.00% | 1.00% |
| Magnesium Stearate | 1.00% | 1.00% | 1.00% | 1.00% | 1.00% |
| HPMC | 0.00% | 0% | 5.00% | 20.00% | 40.00% |
| Total | 100.00% | 100.00% | 100.00% | 100.00% | 100.00% |

Table 2 details the constituents of capsules that contain 50 mg of active ingredient, micronized crystalline (Form A) bardoxolone methyl. In Table 3 this formulation is designated "CTM."

TABLE 2

Composition of bardoxolone methyl capsules containing micronized crystalline form of the drug substance

| Identity | % w/w | mg per capsule |
|---|---|---|
| Bardoxolone Methyl (Micronized) | 18.18 | 50.0 |
| Microcrystalline Cellulose | 18.55 | 51.0 |
| Pregelatinized Starch | 53.45 | 147.0 |
| Copovidone | 8.72 | 24.0 |
| Colloidal Silicon Dioxide | 0.55 | 1.5 |
| Magnesium Stearate | 0.55 | 1.5 |
| Total Capsule Contents | 100.00 | 275 mg |

Pharmacokinetic studies were carried out in fasted cynomolgus monkeys with an average body mass of 3 Kg. In animals treated with the formulations shown in Table 1, a single capsule was administered by oral gavage. In animals treated with the micronized crystalline form as shown in Table 2, two capsules were administered by oral gavage. The dosage of the reference formulation and formulation modifications presented in Table 1 was approximately 10.0 mg/kg, while the dosage of the formulation composition containing the micronized crystalline form of the drug was 33.3 mg/kg.

Blood was withdrawn from each animal, at the time points indicated in FIG. 1, and each sample was quantified for bardoxolone methyl content, using a validated LC/MS/MS bioanalytical test method. The pharmacokinetic data obtained are presented in Table 3.

TABLE 3

Pharmacokinetic parameter estimates from blood obtained following oral capsule administration of 10 mg/kg RTA 402 for each investigated Eudragit formulation and 33 mg/kg RTA 402 crystalline (Form A) CTM [mean (n = 5); pharmacokinetic parameter estimates generated via non-compartmental analysis (WinNonlin ™ software version 5.2)]

| RTA 402 Oral Dose Formulation | ID in Table 1 | $C_{max}$ ng/ml | $T_{max}$ hr | Cl/F L/hr/kg | Cl L/hr/kg | $V_z$/F L/kg | $V_z$ L/kg | $T_{1/2}$ hr | $AUC_{0 \to 72h}$ | % F |
|---|---|---|---|---|---|---|---|---|---|---|
| Eudragit SDD, 0% HPMC | #2 | 27.6 | 6.00 | 25.3 | 3.9 | 467 | 71 | 12.9 | 433 | 15.2 |
| Eudragit SDD, 5% HPMC | #3 | 22.4 | 5.60 | 29.6 | 3.5 | 529 | 63 | 12.4 | 339 | 11.9 |
| Eudragit SDD, 20% HPMC | #4 | 11.4 | 6.40 | 45.5 | 3.7 | 883 | 72 | 13.6 | 230 | 8.1 |
| Eudragit SDD, 40% HPMC | #5 | 16.0 | 10.00 | 36.7 | 3.9 | 797 | 84 | 15.3 | 297 | 10.5 |
| Eudragit SDD, control | #1 | 34.8 | 4.00 | 23.6 | 3.7 | 455 | 71 | 13.4 | 444 | 15.6 |
| Crystalline micronized (Form A), CTM | NA | 10.2 | 12.00 | 126.6 | 3.5 | 2706 | 76 | 14.8 | 258 | 2.8 |

CTM: clinical trial material,
HPMC: hydroxypropyl methylcellulose,
ND: not determined,
SDD: spray dried-dispersion
Pharmacokinetic parameters defined:
$C_{max}$, maximum observed concentration;
$T_{max}$, time of achieved maximum observed concentration;
Cl/F, the apparent oral clearance assuming 100% bioavailability of drug;
Cl, total body clearance of drug corrected for fraction of drug absorbed;
$V_z$/F, the volume of distribution of drug assuming 100% bioavailability of drug, calculated from the terminal phase;
$V_z$, volume of distribution of drug corrected for fraction of drug absorbed and calculated from the terminal phase;
$T_{1/2}$, the estimated pharmacologic half-life of the drug,
$AUC_{0-h}$ is the estimated drug area under the curve from time zero through 72 hours of blood sampling;
% F, percentage of drug absorbed relative to intravenous administration.

FIG. 1 shows that the use of HPMC in a SDD containing Form B bardoxolone methyl (designated "RTA 402") alters the in vivo pharmacokinetic profile of the drug. For instance, increasing concentrations of HPMC lower the mean blood concentration of RTA 402 achieved from a given dose. Thus, a HPMC concentration of 20% w/w lowered the Cmax by >50%, when compared to a control.

Based on the performance of the 5% HPMC formulation described above, in vitro dissolution studies were conducted with formulations of Form B with 2.5%, 5.0%, or 7.5% HPMC, as shown in the table below. The results of these studies suggested that higher percentages of HPMC were associated with slower dissolution rates.

| Components | HPMC 2.5 | HPMC 5.0 | HPMC 7.5 |
|---|---|---|---|
| Bardoxolone methyl SDD | 12.50% | 12.50% | 12.50% |
| Microcrystalline Cellulose | 30.00% | 30.00% | 30.00% |
| Lactose Monohydrate | 50.00% | 47.50% | 45.00% |
| Copovidone XL | 0.00% | 0.00% | 0.00% |
| Sodium Lauryl Sulfate | 3.00% | 3.00% | 3.00% |
| Colloidal Silicon Dioxide | 1.00% | 1.00% | 1.00% |
| Magnesium Stearate | 1.00% | 1.00% | 1.00% |
| HPMC | 2.5% | 5.00% | 7.50% |
| Total | 100.00% | 100.00% | 100.00% |

Figure 2:
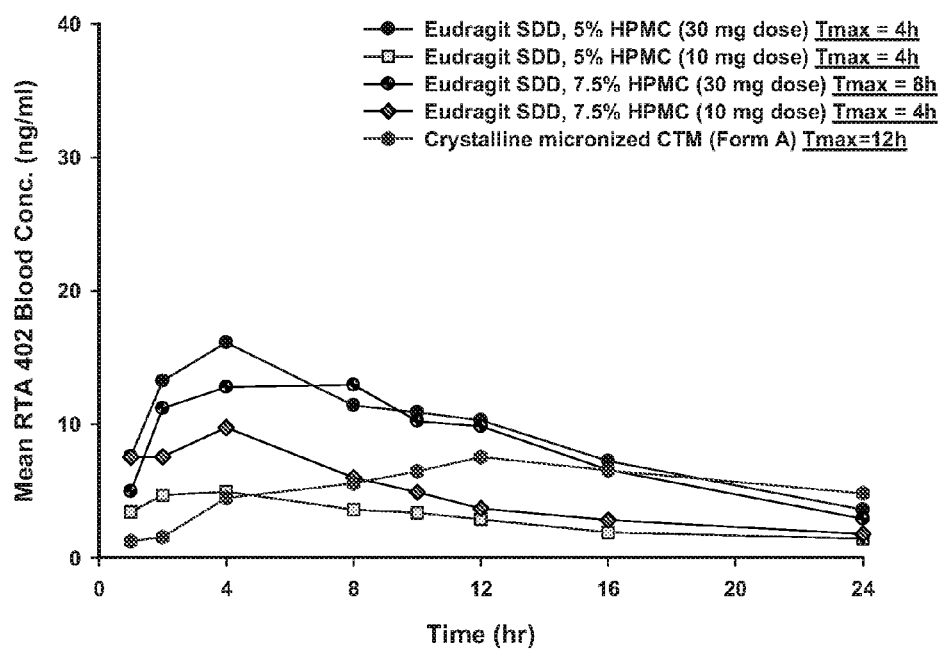
FIG. 2 is a graphical representation of comparative pharmacokinetic data obtained, using cynomolgus monkeys, with different RTA 402 formulations containing 5.0% and 7.5% hydroxypropyl methylcellulose, respectively.

In light of these results, the 5.0% and 7.5% HPMC formulations were selected for comparative pharmacokinetic studies in cynomolgus monkeys, with a control in the form of the crystalline micronized Form A bardoxolone formulation described in Table 2. Each of the HPMC/Form B formulations was administered in capsules, via oral gavage, at doses of either 30 mg or 10 mg. The Form A control formulation was administered at a dose of 100 mg. Results (blood plasma concentration of RTA 402 vs. time) are shown in FIG. 2.

An HPMC formulation containing Form B bardoxolone methyl also was prepared for human clinical studies. Bardoxolone methyl capsules were formulated at 15 mg strength. Table 4 depicts the components used on a per capsule basis. Table 5 presents the composition in a percentage basis.

As described above, the SDD contained 40% bardoxolone methyl active pharmaceutical ingredient (API). As a result, the use of 37.5 mg of SDD per capsule resulted in 15 mg of bardoxolone methyl per capsule.

In Tables 4 and 5, "SMCC" denotes silicified microcrystalline cellulose, a co-processed excipient comprised of compendial excipients. SMCC is listed in the FDA Inactive Ingredients Guide.

TABLE 4

Batch formula for 15 mg strength bardoxolone methyl capsules on a per capsule basis

| Ingredients: | 15 mg mg/Capsule |
|---|---|
| RTA-402 SDD (40% Dispersion of API) | 37.5 |
| SMCC (90LM) | 120 |
| Lactose Monohydrate | 135 |
| Hydroxypropyl methylcellulose | 22.5 |
| Silicon Dioxide Colloidal | 3 |
| Magnesium Stearate | 3 |
| Sodium Lauryl Sulphate | 9 |
| Total Capsule Fill Weight: | 330 mg |
| Capsule Size | #1 |

TABLE 5

Batch formula 15 mg strength bardoxolone methyl capsules on percentage basis

| Ingredients: | 15 mg mg/Capsule |
|---|---|
| RTA-402 SDD (40% Dispersion of API) | 11.36% |
| SMCC (90LM) | 36.36% |
| Lactose Monohydrate | 40.91% |
| Hydroxypropyl methylcellulose | 6.82% |
| Silicon Dioxide Colloidal | 0.91% |

TABLE 5-continued

Batch formula 15 mg strength bardoxolone
methyl capsules on percentage basis

| Ingredients: | 15 mg mg/Capsule |
|---|---|
| Magnesium Stearate | 0.91% |
| Sodium Lauryl Sulphate | 2.73% |
| Total | 100.00% |

To demonstrate that the Form B formulations of the present invention can maintain high bioavailability and achieve the desired PCC in humans, clinical pharmacokinetic studies were carried out in healthy volunteers. The volunteers received a single dose of either 150 mg crystalline bardoxolone methyl (Form A; 3 50 mg capsules) or 30 mg amorphous bardoxolone methyl (Form B; 2 15 mg capsules). Repeated blood samples were subsequently taken and analyzed for plasma concentrations of the drug. After a 10-day washout period, each patient was given the form of the drug that was not administered the first time. A plasma concentration profile was measured again for each patient after the second treatment.

TABLE 6

Summary of pharmacokinetic parameters of the clinical testings

| Patient entry no. | Treatment Period | Dose form | Dose (mg) | $t_{max}$ (h) | $C_{max}$ (ng/mL) | $C_{48h}$ (ng/mL) | $AUC_{0-48h}$ (ng·h/mL) |
|---|---|---|---|---|---|---|---|
| 101 | 1 | Crystalline | 150 | 30.0 | 1.89 | 1.31 | 61.0 |
| 102 | 2 | | | 24.0 | 1.89 | 1.57 | 51.6 |
| 103 | 2 | | | 24.0 | 1.10 | 0.59 | 31.9 |
| 104 | 1 | | | 30.0 | 2.19 | 0.87 | 51.7 |
| 105 | 1 | | | 24.0 | 0.73 | 0.30 | 22.5 |
| 106 | 2 | | | 48.0 | 0.79 | 0.79 | 22.7 |
| | Mean | | | 30.0 | 1.43 | 0.91 | 40.2 |
| | SD | | | 9.3 | 0.63 | 0.47 | 16.6 |
| | CV(%) | | | 31.0 | 44.28 | 51.50 | 41.3 |
| 101 | 2 | Amorphous | 30 | 4.0 | 1.79 | 0.24 | 29.1 |
| 102 | 1 | | | 4.0 | 5.03 | 0.25 | 37.9 |
| 103 | 1 | | | 2.0 | 3.83 | 0.27 | 49.1 |
| 104 | 2 | | | 8.0 | 3.43 | 0.47 | 55.4 |
| 105 | 2 | | | 2.0 | 1.98 | 0.15 [a] | 19.2 |
| 106 | 1 | | | 2.0 | 4.13 | 0.25 | 30.9 |
| | Mean | | | 3.6 | 3.68 | 0.28 | 38.5 |
| | SD | | | 2.6 | 1.12 | 0.12 | 14.4 |
| | CV(%) | | | 72.4 | 30.38 | 42.13 | 37.4 |

[a] Less than the limit of detection

As shown in Table 6, the Form B formulation showed higher bioavailability while achieving an overall exposure profile similar to the crystalline formulation, as measured by the 48 hr AUC values.

In above-described, exemplary compositions of the invention, HPMC illustrates the subclass of cellulose-based binders, including other $C_3$-$C_{10}$ alkyl and aryl substituted cellulose derivatives, that are suitable for use in this context. This subclass of the larger category of hydrophilic binding agents is illustrated as well by methyl cellulose, ethyl cellulose, propyl cellulose, hydroxymethyl cellulose, hydroxypropyl cellulose, hydroxypropyl methyl cellulose, and cellulose acetate.

For purposes of the present invention, preferred as binding agents are alkyl cellulose derivatives, such as hydroxypropyl methyl cellulose, which is commercially available in various molecular weight ranges. Other hydrophilic binding agents also may be used, such as: (a) naturally occurring carbohydrate polymers, e.g., starch and pregelatinized starch; (b) anionic polymers, e.g., acrylic acid homopolymers crosslinked with allyl sucrose or allyl pentaerythritol, (c) polymers of lactic acid or copolymers of lactic and glutamic acid, (d) gelatin or modified gelatins; and (e) amino-substituted carbohydrate polymers, e.g., chitosan.

Without being bound to any particular mechanism or theory, the present inventors believe that the various hydrophilic binding agents discussed above alter the pharmacokinetic profile of amorphous bardoxolone methyl in at least three ways, each contributing to a slower dissolution. First, the hydrophilic material(s), illustrated by HPMC, serves as a binder during the roller compaction process, as described above, to hold the resultant particles together and to form a stronger binding among those primary particles. As a consequence, during dissolution the granules formed by the roller compaction disintegrate more slowly than would be the case otherwise. Second, during dissolution the binder agent or agents form a viscous gel that adheres the Form B-containing particles (and the granules themselves) together, thus further slowing disintegration. Third, the aforementioned viscous gel increases local viscosity in the presence of the dissolution medium. The increase in local viscosity slows diffusion of drug and, hence, dissolution as well.

What is claimed is:

1. A solid dosage form comprising (A) particles consisting of amorphous bardoxolone methyl and a glass-forming excipient admixed with (B) particles consisting of hydroxypropyl methyl cellulose, wherein said particles (A) constitute a therapeutically effective amount of bardoxolone methyl.

2. A solid dosage form comprising (A) particles consisting of amorphous bardoxolone methyl admixed with (B) particles consisting of hydroxypropyl methyl cellulose, wherein said particles (A) constitute a therapeutically effective amount of bardoxolone methyl.

3. The solid dosage form of claim 1, wherein said particles (A) constitute a solid dispersion of amorphous bardoxolone methyl in a glassy matrix.

4. The solid dosage form of claim 3, wherein said particles (A) are the product of a process that comprises spray drying a mixture of bardoxolone methyl and a methacrylic acid copolymer.

5. The solid dosage form of claim 4, wherein said process comprises spray drying a 4:6 mixture of bardoxolone methyl and a methacrylic acid copolymer.

6. The solid dosage form of claim 1 or 2, wherein the proportion of hydroxypropyl methyl cellulose is between about 1% and about 40% (w/w) of the total formulation.

7. The solid dosage form of claim 6, wherein the proportion of hydroxypropyl methyl cellulose is between about 2% and about 20% (w/w) of the total formulation.

8. The solid dosage form of claim 6, wherein the proportion of hydroxypropyl methyl cellulose is between about 4% and about 10% (w/w) of the total formulation.

9. The solid dosage form of claim 6, wherein the proportion of hydroxypropyl methyl cellulose is between about 5% and about 7.5% (w/w) of the total formulation.

10. The solid dosage form of claim 6, wherein the proportion of hydroxypropyl methyl cellulose is between about 7% and about 7.5% (w/w) of the total formulation.

11. The solid dosage form of claim 6, wherein the proportion of hydroxypropyl methyl cellulose is about 7% (w/w) of the total formulation.

\* \* \* \* \*